United States Patent [19]

Taninaka et al.

[11] 4,022,907
[45] May 10, 1977

[54] PHARMACEUTICAL COMPOSITIONS CONTAINING 1,3-DITHIACYCLOALKYLIDENE MALONATES

[75] Inventors: Kuniaki Taninaka, Ibaragi; Hitoshi Kurono, Amagasaki; Tsutomu Kasai, Sakai, all of Japan

[73] Assignee: Nihon Nohyaku Co. Ltd., Tokyo, Japan

[22] Filed: June 6, 1975

[21] Appl. No.: 584,413

[52] U.S. Cl. .............................................. 424/277
[51] Int. Cl.$^2$ ..................................... A61K 31/385
[58] Field of Search ................................... 424/277

[56] References Cited
UNITED STATES PATENTS 3,761,596  9/1973  Taninaka et al. .................. 424/277
3,876,663  4/1973  Taninaka et al. .................. 424/277

Primary Examiner—Frederick E. Waddell
Attorney, Agent, or Firm—Karl W. Flocks

[57] ABSTRACT

A compound having the formula,

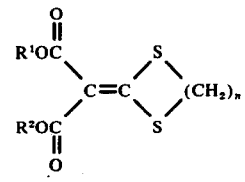

wherein $R^1$ and $R^2$, which may be same or different, represent individually a $C_1$–$C_5$ alkyl group; and $n$ represents an integer of 1, 3 or 4, has effects of stimulating, improving and recovering the functions of livers, and can prevent, alleviate and cure various liver damages of humans and animals when administered either orally or parenterally.

19 Claims, No Drawings

PHARMACEUTICAL COMPOSITIONS CONTAINING 1,3-DITHIACYCLOALKYLIDENE MALONATES

This invention relates to a process for controlling the liver damages of humans and animals, and to a pharmaceutical composition for use in said process.

More particularly, the invention is concerned with a pharmaceutical composition containing an effective amount of a compound represented by the general formula (I),

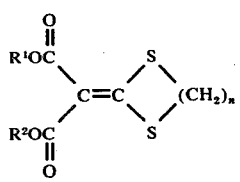

wherein $R^1$ and $R^2$, which may be same or different, represent individually a $C_1$–$C_5$ alkyl group; and $n$ represents an integer of 1, 3 or 4.

The invention further relates to a pharmaceutical composition in the form of administration unit which contains a compound of the above-mentioned general formula (I) as active ingredient, either alone or in admixture with a pharmaceutically acceptable diluent.

The invention further pertains to a process for controlling the liver damages of humans and animals which comprises administering to the humans or animals a pharmaceutical composition in the form of administration unit which contains a compound of the abovementioned general formula (I) as active ingredient, either alone or in admixture with a pharmaceutically acceptable diluent.

The term "controlling the liver damages" or the like, referred to in the body and the claims, means to prevent, alleviate or cure the liver damages.

In view of its various functions, the liver is frequently called a delicate chemical factory. Thus, in the liver, various chemical reactions are being biochemically effected, such as detoxication, sugar metabolism, protein metabolism, lipide metabolism, formation and secretion of bile, control of hormones, formation of blood coagulant prothrombin, regeneration of liver cells, and storage of various living body-constituting elements (fats, glycogens, proteins and vitamins).

However, even such delicate and well-balanced functions of the liver sometime undergo damages, either acutely or chronically, due to various factors such as alcohols, insufficient nutrition, viruses, chemicals, toxicants, etc. to cause such diseases as, for example, hepatitis, jaundice, fatty liver, hepatocirrhosis and liver cancer.

As the result of extensive studies, the present inventors have found that compounds, represented by the aforesaid general formula (I) have actions to activate liver cells and to activate various metabolic functions of the liver, and hence can improve the damaged liver functions to provide such pharmacological effects as to alleviate or cure the damages and to protect the liver functions from certain damages.

An object of the present invention is to provide a novel pharmaceutical composition usable for controlling the liver damages of humans and animals.

Another object of the invention is to provide a process for controlling the liver damages of humans and animals.

Other objects and advantages of the invention will become apparent from the following description.

The compounds represented by the aforesaid general formula (I) partly include known compounds and can be synthesized according to the following reaction scheme:

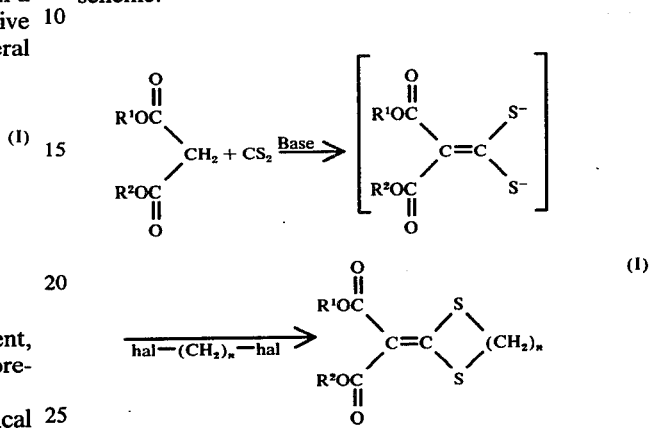

wherein $R^1$, $R^2$ and $n$ are as defined previously, and hal represents a halogen atom.

That is, the compounds of the general formula (I) can be obtained by reacting a malonic acid ester with carbon disulfide in the presence of a suitable base, and then reacting the resulting dithiolate with a dihalogenalkane.

Typical examples of the compounds represented by the general formula (I) are as shown in Table 1.

Table 1

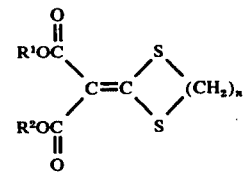

| Compound No. | n | $R^1$ | $R^2$ | m.p. (° C) or b.p. (° C/mmHg) |
|---|---|---|---|---|
| 1 | 1 | $CH_3$ | $CH_3$ | m.p. 158 – 159° C |
| 2 | 1 | $C_2H_5$ | $C_2H_5$ | m.p. 97 – 99° C |
| 3 | 1 | $n\text{-}C_3H_7$ | $n\text{-}C_3H_7$ | m.p. 77.5 – 78° C |
| 4 | 1 | $i\text{-}C_3H_7$ | $i\text{-}C_3H_7$ | m.p. 104 – 105° C |
| 5 | 1 | $n\text{-}C_4H_9$ | $n\text{-}C_4H_9$ | m.p. 51 – 51.5° C |
| 6 | 1 | $n\text{-}C_5H_{11}$ | $n\text{-}C_5H_{11}$ | b.p. 175 – 179° C/0.07 mmHg |
| 7 | 1 | $C_2H_5$ | $i\text{-}C_3H_7$ | m.p. 37 – 39° C |
| 8 | 3 | $CH_3$ | $CH_3$ | b.p. 141 – 146° C/0.07 mmHg |
| 9 | 3 | $C_2H_5$ | $C_2H_5$ | m.p. 60 – 60.5° C |
| 10 | 3 | $n\text{-}C_3H_7$ | $n\text{-}C_3H_7$ | m.p. 42.5 – 43° C |
| 11 | 3 | $i\text{-}C_3H_7$ | $i\text{-}C_3H_7$ | m.p. 95 – 96° C |
| 12 | 3 | $n\text{-}C_4H_9$ | $n\text{-}C_4H_9$ | m.p. 51 – 51.5° C |
| 13 | 3 | $C_2H_5$ | $t\text{-}C_4H_9$ | m.p. 96 – 99° C |
| 14 | 4 | $CH_3$ | $CH_3$ | b.p. 146 – 149° C/0.15 mmHg |
| 15 | 4 | $C_2H_5$ | $C_2H_5$ | m.p. 67.5° C |
| 16 | 4 | $n\text{-}C_3H_7$ | $n\text{-}C_3H_7$ | b.p. 146 – 148° C/0.2 mmHg |
| 17 | 4 | $i\text{-}C_3H_7$ | $i\text{-}C_3H_7$ | m.p. 71 – 73° C |
| 18 | 4 | $n\text{-}C_4H_9$ | $n\text{-}C_4H_9$ | b.p. 158 – 161° C/0.15 mmHg |
| 19 | 4 | $n\text{-}C_5H_{11}$ | $n\text{-}C_5H_{11}$ | b.p. 161 – 164° C/0.2 mmHg |
| 20 | 4 | $C_2H_5$ | $s\text{-}C_4H_9$ | b.p. 141 – 145° C/0.15 mmHg |

The compounds represented by the general formula (I) are extremely low in toxicity to mammals, and their acute oral toxicity to male mice expressed as $LD_{50}$ values are at such a low toxicity level as in the range from 1,000 to 6,000 mg/kg or more, in general. For example the $LD_{50}$ values of the compounds 4, 11 and 17 in Table 1 are more than 5,000 mg/kg. Further, these compounds have no detrimental effects on test animals administered therewith, so far as the doses thereof are within an ordinary administration range.

The compounds of the general formula (I) are usable as pharmaceuticals for humans and animals. They have broad and various pharmaceutical spectra. The compound of the formula (I) has effects of stimulating, improving and recovering the functions of livers, and can prevent, alleviate and cure various liver damages of humans and animals when administered thereto either orally or parenterally. Concretely, they can show in animal tests such main effects as described below.

1. They have effects of preventing, alleviating and curing liver damages (e.g. necrosis, hepatitis, fatty liver) derived from carbon tetrachloride, chloroform, bromobenzene, dimethyl-nitrosoamine, thioacetamide, etc.

2. Accordingly, they are effective for the prevention, alleviation and therapy of liver damages and acute hepatitis due to chemical poisoning.

3. They can prevent, alleviate and cure liver damages derived from administration of ethionine, and hence are effective for prevention, alleviation and therapy of fatty liver diseases.

4. They have actions to stimulate the alcohol metabolic function of the liver to lower the concentration of alcohol in the blood, and hence are effective for promotion of recovery from alcoholic intoxication and for prevention, alleviatation and therapy of crapulence.

5. They have actions to stimulate the sugar metabolic function of the liver to lower the abnormally elevated concentration of sugar in the blood, and hence are effective as blood sugar depressants and curatives for diabetes.

6. When cadmiun or selenium salts are administered to animals, which have previously been administered with the said compounds, the toxic symptoms caused by said salts are far more alleviated than in the case of blank animals.

Accordingly, the compounds represented by the general formula (I) are effective as preventives, alleviatives and curatives for liver damages, acute hepatitis, fatty liver diseases and chemical poisoning. Further, the said compounds are effective as depressants of alcohol in the blood, blood sugar depressants, diabetes curatives, and drugs for stimulating, promoting, improving and recovering metabolic functions of the livers.

In using the said compounds as the abovementioned drugs, they may be formulated, according to usual procedures and means adopted in this field, into pharmaceutical compositions in the form of administration units convenient for their individual application purposes. That is, the said compounds are formulated into pharmaceutical compositions, either alone or in admixture with a pharmaceutically acceptable diluent, which may be any one of solids, semi-solids, liquids and intakable capsules, and are administered to humans or animals, either orally or parenterally.

Thus, the present invention provides a pharmaceutical composition which comprises the abovementioned compound as active ingredient and, in admixture therewith, a pharmaceutically acceptable solid, semisolid or liquid diluent.

The present invention further provides a pharmaceutical composition containing as active ingredient the above-mentioned compound in the form of a sterile and/or isotonic aqueous solution.

The present invention still further provides a pharmaceutical composition in the form of administration unit which contains the above-mentioned compound either alone or in admixture with a pharmaceutically acceptable diluent.

The pharmaceutical compositions of the present invention can be provided in such various administration unit forms as powders, granules, tablets, sugar-coated tablets, pills, capsules, suppositories, suspensions, liquids, emulsions, ampoules and injections.

The present invention includes such mode that the above-mentioned compounds as active ingredient is administered singly. The present invention further includes such mode that the above-mentioned compound is administered in the form of a mixture with a pharmaceutically acceptable diluent. The diluent referred to herein means not only a mere diluent but also a pharmaceutically acceptable usual adjuvant. Examples of the mere diluent are those which are ordinarily used in the pharmaceutical field, and include such solid diluents as starch, lactose, calcium hydrogen phosphate, heavy magnesium oxide and the like, and such liquid diluents as water, isotonic solution, glucose solution and the like. Examples of the adjuvant include vehicles, extenders, binders, wetting agents, disintegrators, surfactants, lubricants, dispersants, buffer agents, seasonings, deodorants, dyes, flavors, preservatives and dissolution aids, though these are not limitative. These adjuvants may be used either singly or in the form of a mixture of two or more members.

The pharmaceutical composition of the present invention may be prepared according to any known method. For example, a mixture of the active ingredient and a diluent is formed, for example, into granules, and the thus formed granular composition is molded, for example, into tablets. In case the pharmaceutical composition is for parenteral administration, it is preferable to be made aseptic and, if necessary, be made isotonic to the blood.

Generally, the pharmaceutical composition of the present invention contains about 0.01 to 100% by weight, based on the weight of the composition, of the active compound. Thus, the present invention includes such mode that the said compound is used independently.

The pharmaceutical composition of the present invention may be incorporated with other pharmaceutically active compound. In some cases, the composition may be incorporated with a plurality of the present compounds.

For the control of various liver damages and various diseases derived therefrom, the pharmaceutical composition of the present invention may be applied according to an ordinary procedure adopted in this field, in order to attain such effects as shown in the aforesaid animal tests. Thus the composition of the present invention is administered orally or parenterally. The oral administration includes sublingual administration, and the parenteral administration includes administration by way of injection including, for example, subcutaneous, intramuscular and intravenous injection.

Effective dose of the present compound is advantageously in the range from 0.1 to 500 mg. per kg. body weight per day in the case of oral administration, and in the range from 0.01 to 250 mg. per kg. body weight per day in the case of parenteral administration. However, the above-mentioned ranges vary depending on the body weight and physical condition of test animal, the manner of administration, the kind and properties of pharmaceutical composition, the time and interval of administration, the kind of disease, etc. Accordingly, in some cases, the dose of the present compound may be made smaller than the minimum dose mentioned above, while in other cases, the dose of the present compound would be in excess of the maximum dose mentioned above. In case the present compound is to be administered in a large dose, it is preferable that the compound is divisionally administered several times a day.

The present invention is illustrated in more detail below with reference to examples including a synthesis example, but the invention is not limited to the examples. In Examples 1 to 8, all parts are by weight.

Synthesis Example 1

Synthesis diisopropyl 1,3-dithiepan-2-ylidene malonate

To a mixture of 20 g (0.1 mole) of diisopropyl malonate and 7.6 g (0.1 mole) of carbon disulfide was added dropwise 30% aqueous solution containing 8.8 g (0.22 mole) of caustic soda while maintaining a temperature at below 20° C. 30 Minutes after stirring at that temperature, the mixture was added with 23.7 g (0.11 mole) of 1,4-dibromobutane, and reacted at a temperature of 50°–70° C for 2 hours. After completion of the reaction, the reaction mixture was poured into 300 ml of ice water to precipitate the objective compound in the form of white crystals. The crystals were obtained by filtration, washed with water, dried, and recrystallized from ether-n-hexane to give 25 g of purified crystals, m.p. 71°–73° C, yield 78.5%.

EXAMPLE 1

| | | |
|---|---|---|
| Di-n-propyl 1,3-dithietan-2-ylidene malonate (Compound 3) | 10 | parts |
| Heavy magnesium oxide | 10 | " |
| Lactose | 80 | " |

The above-mentioned components were homogeneously mixed and pulverized to obtain a powder.

EXAMPLE 2

| | | |
|---|---|---|
| Diisopropyl 1,3-dithietan-2-ylidene malonate (Compound 4) | 10 | parts |
| Synthetic aluminum silicate | 10 | " |
| Calcium hydrogenphosphate | 5 | " |
| Lactose | 75 | " |

The above-mentioned components were treated in the same manner as in Example 1 to obtain a powder.

EXAMPLE 3

| | | |
|---|---|---|
| Diisopropyl 1,3-dithian-2-ylidene malonate (Compound 11) | 50 | parts |
| Starch | 10 | " |
| Lactose | 15 | " |
| Crystalline cellulose | 20 | " |
| Polyvinyl alcohol | 5 | " |
| Water | 30 | " |

The above-mentioned components were homogeneously kneaded, granulated, dried and sieved to obtain a granule.

EXAMPLE 4

99 Parts of the granule obtained in Example 3 was incorporated with 1 part of calcium stearate, and then subjected to compression molding to obtain a tablet of 10 mm. in diameter.

EXAMPLE 5

| | | |
|---|---|---|
| Di-n-propyl 1,3-dithian-2-ylidene malonate (Compound 10) | 95 | parts |
| Polyvinyl alcohol | 5 | " |
| Water | 30 | " |

The above-mentioned components were treated in the same manner as in Example 3 to obtain a granule. 90 Parts of the thus obtained granule was incorporated with 10 parts of crystalline cellulose, and then subjected to compression molding to obtain a tablet of 8 mm. in diameter. Further, this tablet was formed into a sugar-coated tablet by use of proper amounts of a suspension comprising ethanolic shellac, syrup gelatin and precipitated calcium carbonate, and a dye.

EXAMPLE 6

| | | |
|---|---|---|
| Compound 4 | 4 | parts |
| Nonionic surfactant | 10 | " |
| Isotonic sodium chloride solution | 86 | " |

The above-mentioned components were mixed together with heating to form a solution, which was then cooled to obtain an injection.

EXAMPLE 7

| | | |
|---|---|---|
| Compound 11 | 0.5 | part |
| Nonionic surfactant | 2.5 | parts |
| Distilled water for injection | 97.0 | " |

The above-mentioned components were treated in the same manner as in Example 6 to obtain an injection.

EXAMPLE 8

The power obtained in Example 1 was filled into commercially available capsules to obtain a capsule.

EXAMPLE 9

Protection against $CCl_4$-induced Hepatotoxicity:

Carbon tetrachloride ($CCl_4$) administration induces centrilobular necrosis of the liver associated with loss of diphosphopyridine nucleotide, hepatic glycogen, coenzyme A and increase in neutral fat. Release of several enzymes from the hepatocytes, and increase of enzyme activities in the plasma are recognized as the result of the damage of the liver. A suitable means for evaluating the degree of damage induced by $CCl_4$ or the degree of protection afforded by drugs is to study the plasma glutamic-pyruvic transaminase(p-GPT) activity.

Methods: The test compounds were dissolved or suspended in olive oil and administered orally at the dose of 250 mg/kg to the mice (Four-week-old male mice-dd strain). After 6 hours, $CCl_4$ was administered orally (0.05 ml/kg as olive oil solution). Animals were killed 24 hours after $CCl_4$ administration, and the liver was grossly observed. The plasma was obtained by centrifugation. Activities of p-GPT were determined by the method of Reitman and Frankels and expressed in Karmen units. Score for liver damage index was as follows:

| Liver damage index | Description |
|---|---|
| 0 | Normal |
| 2 | Slightly recognized |
| 4 | Clearly observable damage |
| 6 | Heavy damage |

| Liver damage index | Description |
|---|---|
| 0 | Normal |
| 2 | Slightly recognized |
| 4 | Clearly observable damage |
| 6 | Heavy damage |

Each figure indicates average of 5 to 6 mice. Values of p-GPT over 1,000 Karmen unit regarded as 1,000 for calculation of average for convenience.

Results:

Table 2

| Compound No. | Liver damage index | p-GPT |
|---|---|---|
| 1 | 1.5 | 341 |
| 2 | 0.3 | 29 |
| 3 | 0.2 | 22 |
| 4 | 0.0 | 20 |
| 5 | 1.2 | 158 |
| 6 | 1.2 | 167 |
| 7 | 0.6 | 54 |
| 8 | 2.8 | 437 |
| 9 | 2.2 | 366 |
| 10 | 2.2 | 50 |
| 11 | 2.3 | 215 |
| 12 | 1.8 | 284 |
| 13 | 1.4 | 125 |
| 14 | 3.5 | 762 |
| 15 | 3.2 | 533 |
| 16 | 3.0 | 710 |
| 17 | 3.6 | 688 |
| 18 | 0.5 | 41 |
| 19 | 0.7 | 157 |
| 20 | 1.0 | 188 |
| Carbon tetrachloride alone | 5.2 | >1,000 |
| Thioctic acid amide | 4.8 | 763 |
| Anetol trithion | 1.6 | 38 |
| Control | 0 | 35 |

Carbon tetrachloride is best suitable for bringing test animals to the state of acute hepatitis. As is clear from the results of tests carried out by use of carbon tetrachloride, all the active ingredients used in the present composition show prominent liver damage-preventing effects, and are comparable in effectiveness to thioctic acid amide and anethol tritiion which are commercially available at present as liver drugs.

EXAMPLE 10

Therapeutic effect against thioacetamide-induced hepatotoxicity

Thioacetamide (hereinafter abbreviated to "TAA") also causes liver damages in animals, like carbon tetrachloride, and hence is frequently used as a chemical for bringing about hepatitis and fatty liver diseases. In the tests of this Example, TAA was repeatedly administered to animals to prepare test animals suffering from somewhat chronic liver damages, and then the present compounds were administered thereto to know whether or not the compounds were effective against chronic hepatitis.

The degree of the liver damage and the therapeutic effects of the compounds were evaluated according to BSP test. The BSP test is a method in which BSP (sulfobromophthalein sodium), a dye known to be quickly metabolized in and excreted from the liver, is intravenously injected into animals and, after a definite period of time, the blood is taken out to measure the amount of BSP remaining in the plasma. In case the animals are suffering from the liver damage, the dye will remain, according to the degree of the damage, at the stage where a major portion of BSP is metabolized and excreted in the case of normal animals. Five groups of rats (Sprague Dawley strain) were treated as follows:

Group A: The rats were orally administered with 100 mg/kg of thioacetamide, at 3 days intervals for 36 days (12 times of the administration), then were submitted for 10 days to a normal diet.

Group B: The rats were orally administered with 100 mg/kg of thioacetamide at 3 days intervals for 36 days (12 times of the administration), then were submitted for 10 days to the normal diet + 0.2% of compound 4.

Group C: The rats were orally administered with 100 mg/kg of thioacetamide at 3 days intervals for 36 days (12 times of the administration) then were submitted for 10 days to the normal diet + 0.2% of compound 2.

Group D: The rats were orally administered with 100 mg/kg of thioacetamide at 3 days intervals for 36 days((12 times of the administration) then were submitted for 10 days to the normal diet + 0.2% of anethol trithion.

Group E: The rats were submitted to the normal diet as the control.

Five rate were sacrificed from each group at appropriate intervals for BSP (sulfobromophthalein) test, the results of which were shown as amounts (mg) of BSP remaining in 1 dl of plasma.

Table 3

| Time of Sacrifice | Group A | Group B | Group C (mg/dl) | Group D | Group E |
|---|---|---|---|---|---|
| 24hr after 4 times TAA administration | | 18.2 ± 2.6 | | | 0.3±0.1 |
| 24hr after 8 times TAA administration | | 16.8 ± 5.2 | | | — |
| 24hr after 12 times TAA administration | | 17.3 ± 4.4 | | | 0.8±0.1 |
| After compounds administration | | | | | |
| 2 days | 12.7±3.7 | 7.1±0.8 | 7.5±1.2 | 9.7±4.1 | 0.4±0.1 |
| 5 days | 8.7±1.9 | 3.2±0.6 | 3.8±0.4 | 7.3±3.4 | — |

Table 3-continued

| Time of Sacrifice | Group A | Group B | Group C (mg/dl) | Group D | Group E |
| --- | --- | --- | --- | --- | --- |
| 10 days | 1.4±0.4 | 0.6±0.2 | 0.7±0.1 | 0.9±0.1 | 0.6±0.1 |

By the repeated administration of TAA, the concentration of BSP in the blood increased to 16 to 19 mg/dl and the said level lasted, and therefore it is considered that the rats were brought to a state close to chronic hepatitis. After the administration of TAA, the present compound-administered groups (Groups B and C) were quicker in cure of liver damage than the unadministered group (Group A). This indicates that the present compounds are effective against chronic hepatitis as well.

EXAMPLE 11

Effect of Concentration of Ethylalcohol in the Blood:

The test compounds are dissolved or suspended in olive oil and administered orally at the dose of 250 mg/kg to the mice. After 6 hours, 1,000 mg/kg of ethylalcohol was given orally. Blood was taken in a capillary from caudal vein at the time indicated in the results. The plasma was obtained by centrifugation. The concentration of ethylalcohol in the plasma was measured by FID type gas liquid chromatography. Five mice were used for each group.

Table 4

| | Results Concentration of Ethylalcohol in Plasma (ppm.) | | | | |
| --- | --- | --- | --- | --- | --- |
| Time (min.) | Control | Compound Pre-treated | | | |
| | | Compound 2 | Compound 4 | Compound 10 | Compound 20 |
| 0 | 27 ± 17 | 11 ± 4 | 10 ± 3 | 13 ± 4 | 15 ± 2 |
| 5 | 875 ± 203 | 714 ± 167 | 695 ± 122 | 753 ± 78 | 710 ± 134 |
| 15 | 810 ± 191 | 655 ± 102 | 637 ± 113 | 698 ± 95 | 652 ± 143 |
| 30 | 690 ± 214 | 426 ± 101 | 410 ± 77 | 451 ± 114 | 404 ± 93 |
| 60 | 167 ± 76 | 15 ± 10 | 15 ± 8 | 12 ± 11 | 18 ± 6 |
| 120 | 5 ± 1 | N.D. (Not detected) | N.D. | N.D. | N.D. |

The concentration of ethyl alcohol in the plasma of the present compound-treated mice was lower than that of normal mice. This tendency was particularly marked at the stages of 30, 60 and 120 minutes after administration of ethyl alcohol, and thus it is understood that the amount of ethyl alcohol in the treated mice decreased quickly. Further, the present compound-treated mice were obviously quicker in recovery of intoxicated state, when observed visually. This indicates that by administration of the present compounds, the mice were stimulated in alcohol metabolic function of liver.

EXAMPLE 12

Effect on glucose metabolism:

Methods: The test compounds dissolved in olive oil and administered orally at the dose of 250 mg/kg to the mice. After 6 hours, 4.0 g/kg of glucose was orally administered. The same amount of glucose was given to the control animals. 0.02 ml of blood was taken from caudal vein of the mice at 30, 60, 90 and 120 min. after glucose administration. Blood sugar was measured by the procedure of SomogyiNelson. Number of animals used was 5 to 6 mice for each treatment.

Table 5

| | Results Blood Sugar (mg/dl) | | | |
| --- | --- | --- | --- | --- |
| Time (min.) | Control | Test compound Pre-treatment | | |
| | | Compound 2 | Compound 4 | Compound 10 |
| 0 | 145 ± 11.8 (100%) | 142 ± 22.8 | 168 ± 20.4 | 148 ± 14.7 |
| 30 | 311 ± 21.9 (214%) | 258 ± 17.5 | 280 ± 10.8 | 267 ± 21.2 |
| 60 | 290 ± 14.6 (200%) | 229 ± 18.7 | 215 ± 20.1 | 222 ± 18.3 |
| 90 | 263 ± 13.1 (181%) | 183 ± 18.1 | 164 ± 16.5 | 162 ± 14.4 |
| 120 | 251 ± 13.5 (173%) | 150 ± 20.4 | 165 ± 15.3 | 148 ± 18.8 |

The blood sugar values of the each group showed peaks after 30 minutes, and no substantial difference was seen in the peak values. Thereafter, however, obvious difference was observed in the recovery of blood sugar value, and the present compound-treated groups were quicker in recovery. This indicates that by administration of the present compounds, the mice were stimulated in glucose metabolic function of liver.

What is claimed is:

1. A process for preventing or curing fatty liver or hepatitis, preventing liver necrosis or lowering abnormally elevated concentrations of sugar or alcohol in the blood, of animals including humans, which comprises
orally or parenterally administering to a said animal in need of said therapy or prevention, a therapeutic effective amount of a compound having the general formula,

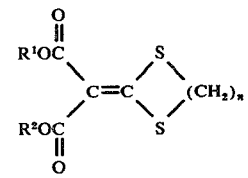

wherein $R^1$ and $R^2$, which may be same or different, represent individually a $C_1$-$C_5$ alkyl group and $n$ represents an integer of 1, 3 or 4.

2. The process of claim 1, wherein the administration is carried out parenterally.

3. The process of claim 2, wherein the dose is in the range from 0.01 to 250 mg. per kg. body weight per day.

4. The process of claim 1, wherein the administration is carried out orally.

5. The process of claim 4, wherein the dose is in the range from 0.1 to 500 mg. per kg. body weight per day.

6. The process of claim 1, wherein the compound is diisopropyl 1,3-dithietan-2-ylidene malonate.

7. The process of claim 1, wherein the compound is di-n-propyl 1,3-dithietan-2-ylidene malonate.

8. The process of claim 1, wherein the compound is diisopropyl 1,3-dithian-2-ylidene malonate.

9. The process of claim 1, wherein the compound is administered for stimulating the alcohol metabolic function of liver to lower the concentration of alcohol in the blood.

10. The process of claim 9, wherein the compound is diisopropyl 1,3-dithietan-2-ylidene malonate.

11. The process of claim 9, wherein the compound is di-n-propyl 1,3-dithietan-2-ylidene malonate.

12. The process of claim 9, wherein the compound is diisopropyl 1,3-dithian-2-ylidene malonate.

13. The process of claim 1 for treating diabetes in an animal, wherein the compound is orally administered in an effective blood-sugar depressant amount to said animal for stimulating the sugar metabolic function of liver to lower the abnormally elevated concentration of sugar in the blood.

14. The process of claim 13, wherein the compound is diisopropyl 1,3-dithietan-2-ylidene malonate.

15. The process of claim 13, wherein the compound is di-n-propyl 1,3-dithietan-2-ylidene malonate.

16. The process of claim 13, wherein the compound is diisopropyl 1,3-dithian-2-ylidene malonate.

17. The process of claim 1 for the treatment of liver necrosis, fatty liver or hepatitis, wherein the compound is administered to said animal in an amount effective to alleviate said necrosis, fatty liver or hepatitis.

18. The process of claim 17, wherein said necrosis, fatty liver or hepatitis is induced by chemical poisoning.

19. The process of claim 18, wherein said chemical poisoning is caused by carbon tetrachloride, chloroform bromobenzene, dimethyl-nitrosaimine, thioacetamide, ethionine, a cadmium salt or a selenium salt.

* * * * *